United States Patent [19]

Baker

[11] Patent Number: 5,428,484
[45] Date of Patent: Jun. 27, 1995

[54] MOVEABLE HAND-HELD LIGHTED MIRROR

[76] Inventor: Michael W. Baker, 894 Mohawk Dr., Livermore, Calif. 94550

[21] Appl. No.: 289,508

[22] Filed: Aug. 12, 1994

[51] Int. Cl.⁶ .................. G02B 7/182; F21V 33/00
[52] U.S. Cl. ............................ 359/872; 359/881; 359/882; 362/139; 362/142
[58] Field of Search ............... 359/872, 881, 882; 362/135, 138, 139, 142, 203

[56] References Cited

U.S. PATENT DOCUMENTS

| | | | |
|---|---|---|---|
| 938,525 | 11/1909 | Turney | 362/138 |
| 1,036,000 | 8/1912 | Pease | 359/882 |
| 1,638,986 | 8/1927 | De Zeng | 362/139 |
| 1,656,754 | 1/1928 | Norris | 362/139 |
| 1,750,194 | 3/1930 | Rydman | 359/882 |
| 1,817,417 | 8/1931 | Meitzler | 362/139 |
| 2,107,791 | 2/1938 | Henning | 362/138 |
| 2,222,879 | 11/1940 | Porter | 362/138 |

Primary Examiner—Ricky D. Shafer
Attorney, Agent, or Firm—Robert J. Harter

[57] ABSTRACT

A hand held telescoping mirror device includes a light bulb situated to provide a broad illumination region. The device includes several useful features such as a telescoping arm that retracts within the handle, a twist type on-off switch, and a mirror that's interchangeable with a magnifying glass. In addition, the handle and telescoping arm are separable from the rest of the device so that they may be reconnected to various accessories such as a brush or magnet.

12 Claims, 2 Drawing Sheets

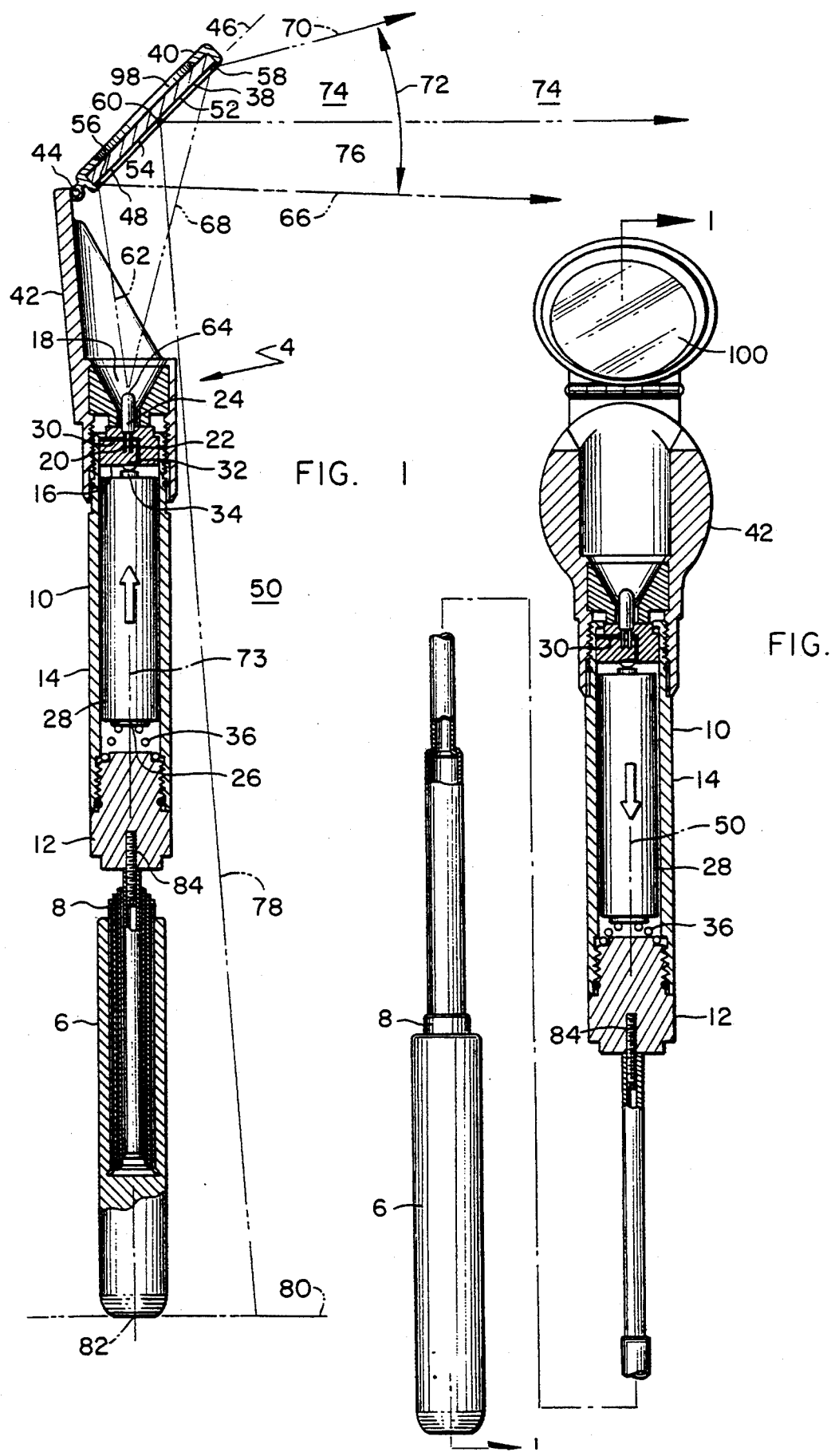

MOVEABLE HAND-HELD LIGHTED MIRROR

BACKGROUND OF THE INVENTION

1. Field Of The Invention

The subject invention generally pertains to a moveable hand-held mirror, and more specifically to one having a telescoping 2. Description Of Related Art Hand held telescoping mirrors are often used along with a flashlight. However, it is often difficult to both see and illuminate an object through a mirror simultaneously. This is because the object is best illuminated by placing the flashlight directly in the line of sight which blocks one's view. In addition, a mirror in one hand and a flashlight in the other, leaves one without a hand free to work on the object being viewed.

SUMMARY OF THE INVENTION

To avoid the limitations and problems with today's hand held telescoping mirrors, it is an object of the invention to illuminate an object with reflected light off a mirror without obstructing one's view.

Another object is to provide a mirror, bulb, and battery assembly that is disconnectable as a unit from a telescoping arm to allow accessories to be mounted in their place.

Another object is to provide a mirror housing that interchangeably receives a mirror and a magnifying glass.

Another object is to strategically locate a light bulb near a pivotable mirror such that the illuminated area encompasses a line of sight over a broad range of pivot positions of the mirror.

Another object is to incorporate a twist type switch in a telescoping mirror.

Another object is to provide a lighted telescoping mirror having its line of sight entirely beyond its exterior.

These and other objects of the invention are provided by a novel hand held telescoping lighted mirror device. The device includes a bulb and mirror arrangement that provides a reflected illuminated region that fully encompasses an unobstructed line of sight outside a telescoping arm.

BRIEF DESCRIPTION OF THE DRAWING

FIG. 1 is a cross-sectional view of the subject invention with the sheet representing a reference plane. The view is taken across line 1—1 of FIG. 2 with the exceptions of a mirror instead of a magnifying glass, the switch on instead of off, and the telescoping arm retracted instead of extended.

FIG. 2 is another cross-sectional view of the subject invention.

DESCRIPTION OF THE PREFERRED EMBODIMENT

Figure 3:
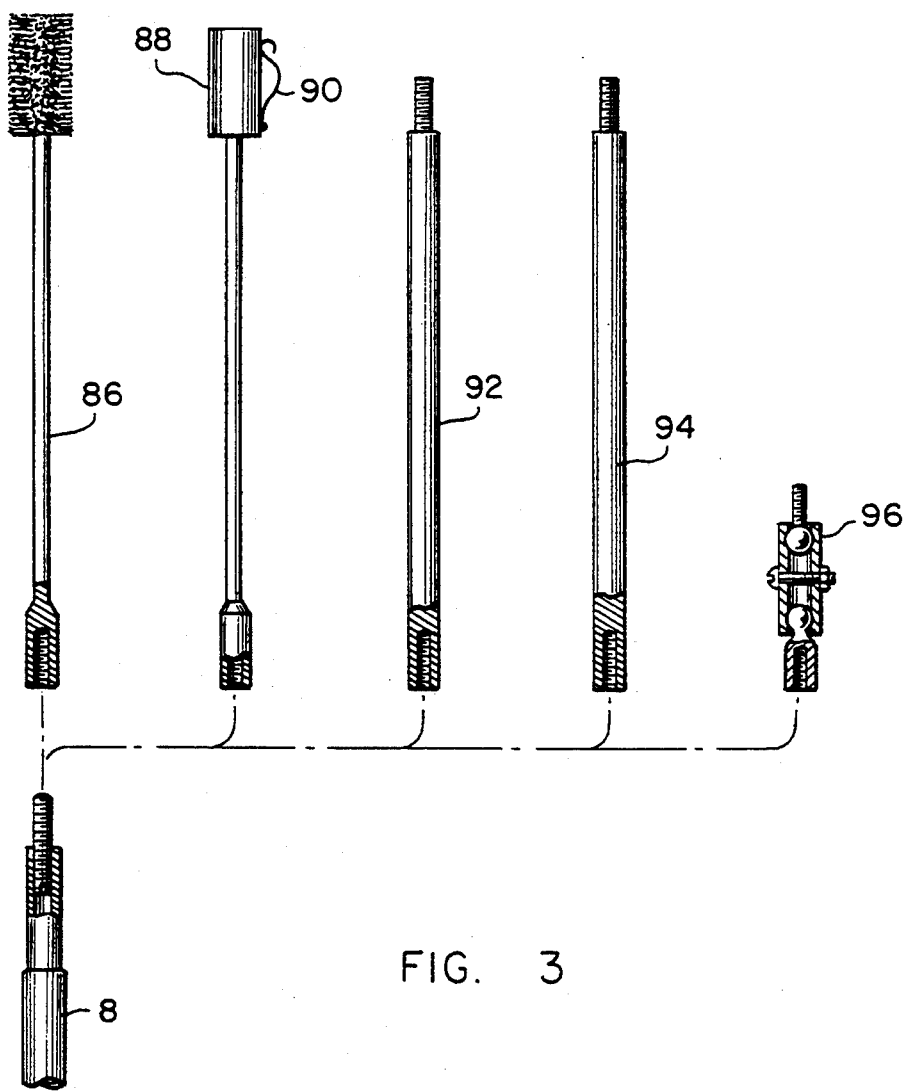
FIG. 3 illustrates various accessories.

Referring to FIG. 1, a lighted mirror 4 includes a hollow handle 6 attached to a telescoping arm 8. Telescoping arm 8 extends and retracts like an antenna and in FIG. 1 is shown in the retracted position. Arm 8 is attached to a battery compartment 10 which includes an electrically conductive battery cap 12, an electrically conductive cylindrical tube 14 with an outer electrically insulated coating, and a bulb socket 16. An incandescent light bulb 18 engages socket 16 by way of two electrical leads 20 and 22 extending from its base 24. Lead 20 is connected to a negative pole 26 of a battery 28 via a conductor 30, tube 10 spring 36, and cap 12. Lead 22 is connected to a positive pole 34 of battery 28 via conductor 32. A round mirror 38, held in a mirror casing 40, is pivotally coupled to arm 8 and battery compartment 10 by way of a light casing 42 that screws onto tube 14 and is pivotally connected to mirror casing 40 by way of a hinge 44. FIG. 1 shows an obstructed pivot range of at least 90 degrees.

Light casing 42, tube 14, and bulb socket 16 together serve as a twist activated light switch. The extent to which light casing 42 is screwed onto tube 14 determines whether light bulb 18 is energized (on) or de-energized (off). When light casing 42 is screwed out as shown in FIG. 1, conductor 30 becomes electrically connected to negative pole 26 to complete the circuit to energize light bulb 18. When light casing 42 is screwed in as shown in FIG. 2, the electrical connection between conductor 30 and tube 14 is broken to turn off light bulb 18.

Battery compartment 10 can be opened to change battery 28 by unscrewing battery cap 12.

The mechanical arrangement of the components of lighted mirror 4 can be described with imaginary planes, optical lines, and points of reference. A mirror line 46 is defined as the line of intersection of a mirror plane 48 and a reference plane 50. Mirror plane 48 lies across a front face side 52 of mirror 38. Reference plane 50 lies parallel to the page of FIG. 1, runs substantially along the length and center of arm 8, and is substantially perpendicular to mirror plane 48. Within mirror line 46 is a mirror line segment 54 that extends from one fully exposed edge of mirror 38 at a proximal point 56 to a substantially opposite fully exposed edge of mirror 38 at a distal point 58. Halfway between proximal point 56 and distal point 58 is a mirror center point 60.

A first incident line 62 extends from a bulb tip point 64 to proximal point 56 and reflects off mirror 38 to produce a first reflected line 66. A second incident line 68 extends from bulb tip point 64 to distal point 58 and reflects off mirror 38 to provide a second reflected line 70. Bulb tip point 64 is spaced apart from mirror center point 60 at a distance of less than five times the length of mirror line segment 54 so that first reflected line 66 and second reflected line 70 diverge at least 10 to 20 degrees (angle of divergence 72) when mirror plane 48 is at a 45° angle to a longitudinal centerline 73 of arm 8. In one embodiment of the invention, the distance from bulb tip point 64 to mirror center point 60 is 1.7 inches. This provides an adequate illumination area 74 to encompass a reflected line of sight 76 running from mirror center point 60 and extending outward for a distance at least five times the length of mirror line segment 54. Reflected line of sight 76 corresponds to an unobstructed incident line of sight 78 running from mirror center point 60 to an eye line 80. Incident line of sight 78 lies in reference plane 50 and is as closely parallel to longitudinal centerline 73 as possible without being obstructed by any opaque parts of lighted mirror 4. Eye line 80 is defined as a line perpendicular to longitudinal centerline 73, lying in reference plane 50, and passing through handle 6 at a point 82 furtherest away from mirror center point 60 when telescoping arm 8 is fully retracted as shown in FIG. 1.

Telescoping arm 8 is selectively disconnectable from battery compartment 10 by way of a threaded connection 84. This allows telescoping arm 8 to be selectively coupled to an accessory. Examples of an accessory include but are not limited to a brush 86, a magnet 88 or clip 90, a rigid extension 92, a flexible extension 94, and a universal joint 96 (see FIG. 3). Extensions 92, 94 and universal joint 96 are meant to be used in conjunction with another accessory or reconnected to battery compartment 10.

As an added feature, mirror casing 40 has an open, see-through portion 98 so that a magnifying glass 100 can be selectively used in place of mirror 38.

Although the invention is described with respect to a preferred embodiment, modifications thereto will be apparent to those skilled in the art. Therefore, the scope of the invention is to be determined by reference to the claims which follow.

I claim:

1. A compact pocket-size portable hand-held moveable mirror device lying across a reference plane and being adapted to be powered by a battery, said device comprising:

a hollow handle;

a telescoping arm having a first end and a second end with said first end being attached to said handle, said telescoping arm having an interior, an exterior, and a longitudinal center line, said longitudinal center line being substantially parallel to said reference plane, said telescoping arm having a portion that telescopes within said handle;

a mirror coupled to said telescoping arm at said second end of said telescoping arm, said mirror having a face side lying substantially in a mirror plane, said mirror plane being perpendicular to and intersecting said reference plane to define a mirror line having a mirror line segment extending from one exposed edge of said mirror at a proximal point to a substantially opposite exposed edge of said mirror at a distal point with a mirror center point midway between said proximal point and said distal point, said mirror being pivotally adjustable relative to said longitudinal center line to a position where said mirror plane is at a 45 degree angle to said longitudinal center line; and a light bulb having a base at one end of said light bulb and a bulb tip point at an opposite end of said light bulb, said base serving as an electrical contact, said bulb tip point lying in said reference plane and being disposed between said mirror and said telescoping arm, said bulb tip point and said proximal point defining a first incident line corresponding to a first reflected line, said bulb tip point and said distal point defining a second incident line corresponding to a second reflected line whereby said first reflected line and said second reflected line diverge to border an illumination region in front of said face side of said mirror, said bulb tip point being spaced apart from said mirror center point at a distance of less than 5 times the length of said mirror line segment to provide an angle of divergence between said first reflected line and said second reflected line of at least 10 degrees to encompass a reflected line of sight extending from said mirror center point outward to a distance of at least 5 times the length of said mirror line segment with said reflected line of sight corresponding to an unobstructed incident line of sight lying beyond said exterior of said telescoping arm and originating from an eye line and extending to said mirror center point, said eye line being defined as a line perpendicular to said longitudinal center line, parallel to said reference plane, and passing through said handle at a point furthest way from said mirror center point when said telescoping arm is fully retracted.

2. The device of claim 1 wherein said bulb tip point is spaced apart from said mirror center point at a distance of less than twice the length of said mirror line segment to make said angle of divergence at least 20 degrees.

3. The device of claim 1, wherein said mirror is coupled to said telescoping arm by way of a battery compartment adapted to hold said battery.

4. The device of claim 3 wherein said telescoping arm is selectively separable from said mirror to provide access to an interior of said battery compartment.

5. The device of claim 3 wherein said battery compartment is adapted to hold said battery substantially coaxially aligned with said longitudinal center line.

6. The device of claim 1 further comprising a twist actuated switch.

7. The device of claim 1 wherein said mirror is pivotally adjustable over an adjustment range of at least 90 degrees by way of a hinge that couples said mirror to said telescoping arm.

8. A compact pocket-size portable hand-held moveable device lying across a reference plane and being adapted to be powered by a battery, said device comprising:

a hollow handle;

a telescoping arm having a first and a second end with said first end being attached to said handle, said telescoping arm having an interior, an exterior, and a longitudinal center line, said longitudinal center line being substantially parallel to said reference plane, said telescoping arm having a portion that telescopes within said handle;

a battery compartment attached to said second end of said telescoping arm, said battery compartment being adapted to hold said battery;

a mirror coupled to said battery compartment, said mirror having a face side lying substantially in a mirror plane, said mirror plane being perpendicular to and intersecting said reference plane to define a mirror line having a mirror line segment extending from one exposed edge of said mirror at a proximal point to a substantially opposite exposed edge of said mirror at a distal point with a mirror center point midway between said proximal point and said distal point, said mirror being pivotally adjustable relative to said longitudinal center line to a position where said mirror plane is at a 45 degree angle to said longitudinal center line; and a light bulb having a base at one end of said light bulb and a bulb tip point at an opposite end of said light bulbs said base serving as an electrical contact, said bulb tip point lying in said reference plane and being disposed between said mirror and said telescoping arm, said bulb tip point and said proximal point defining a first incident line corresponding to a first reflected line, said bulb tip point and said distal point defining a second incident line corresponding to a second reflected line whereby said first reflected line and said second reflected line diverge to border an illumination region in front of said face side of said mirror, said bulb tip point being spaced apart from said mirror center point at a distance of less than twice the length of said mirror line segment to provide an angle of divergence between said first reflected line and said second reflected line of at least 20 degrees to fully encompass a reflected line of sight extending from said mirror center point outward to a distance of at least 5 times the length of said mirror line segment with said reflected line of sight corresponding to an unobstructed incident line of sight lying beyond said exterior of said telescoping arm and originating from an eye line and extending to said mirror center point, said eye line being defined as a line perpendicular to said longitudinal center line, parallel to said reference plane, and passing through said handle at a point furthest away from said mirror center point when said telescoping arm is fully retracted.

9. The device of claim 8 wherein said battery compartment is adapted to hold said battery substantially coaxially aligned with said longitudinal center line.

10. The device of claim 8 further comprising a twist actuated switch.

11. The device of claim 8 wherein said mirror is pivotally adjustable over an adjustment range of at least 90 degrees by way of a hinge that couples said mirror to said telescoping arm.

12. A compact pocket-size portable hand-held moveable mirror device lying across a reference plane and being adapted to be powered by a battery, said device comprising:

a hollow handle;

a telescoping arm having a first and a second end with said first end being attached to said handle, said telescoping arm having an interior, an exterior, and a longitudinal center line, said longitudinal center line being substantially parallel to said reference plane, said telescoping arm having a portion that telescopes within said handle;

a battery compartment attached to said second end of said telescoping arm, said battery compartment being adapted to hold said battery substantially coaxially aligned with said longitudinal center line;

a twist activated switch coupled to said battery compartment;

a mirror coupled to said battery compartment by way of a hinge that renders said mirror pivotally adjustable over an adjustment range of at least 90 degrees, said mirror having a face side lying substantially in a mirror plane, said mirror plane being perpendicular to and intersecting said reference plane to define a mirror line having a mirror line segment extending from one exposed edge of said mirror at a proximal point to a substantially opposite exposed edge of said mirror at a distal point with a mirror center point midway between said proximal point and said distal point, said mirror being pivotally adjustable relative to said longitudinal center line to a position where said mirror plane is at a 45 degree angle to said longitudinal center line; and a light bulb having a base at one end of said light bulb and a bulb tip point at an opposite end of said light bulb, said base serving as an electrical contact, said bulb tip point lying in said reference plane and being disposed between said mirror and said telescoping arm, said bulb tip point and said proximal point defining a first incident line corresponding to a first reflected line, said bulb tip point and said distal point defining a second incident line corresponding to a second reflected line whereby said first reflected line and said second reflected line diverge to border an illumination region in front of said face side of said mirror, said bulb tip point being spaced apart from said mirror center point at a distance of less than twice the length of said mirror line segment to provide an angle of divergence between said first reflected line and said second reflected line of at least 20 degrees to fully encompass a reflected line of sight extending from said mirror center point outward to a distance of at least 5 times the length of said mirror line segment with said reflected line of sight corresponding to an unobstructed incident line of sight lying beyond said exterior of said telescoping arm and originating from an eye line and extending to said mirror center point, said eye line being defined as a line perpendicular to said longitudinal center line, parallel to said reference plane, and passing through said handle at a point furthest away from said mirror center point when said telescoping arm is fully retracted.

* * * * *